United States Patent
Wu et al.

(10) Patent No.: US 11,344,406 B2
(45) Date of Patent: May 31, 2022

(54) CAM-ACTUATED OPTIC LOCKOUT MECHANISM

(71) Applicant: Alcon Inc., Fribourg (CH)

(72) Inventors: Yinghui Wu, Cedar Hill, TX (US); Len Takudzwa Magara, Fort Worth, TX (US); Douglas Brent Wensrich, Bedford, TX (US)

(73) Assignee: Alcon Inc., Fribourg (CH)

( * ) Notice: Subject to any disclaimer, the term of this patent is extended or adjusted under 35 U.S.C. 154(b) by 183 days.

(21) Appl. No.: 16/712,164

(22) Filed: Dec. 12, 2019

(65) Prior Publication Data

US 2020/0197162 A1 Jun. 25, 2020

Related U.S. Application Data

(60) Provisional application No. 62/782,804, filed on Dec. 20, 2018.

(51) Int. Cl.
 *A61F 2/02* (2006.01)
 *A61F 2/16* (2006.01)

(52) U.S. Cl.
 CPC ........ *A61F 2/167* (2013.01); *A61F 2250/006* (2013.01)

(58) Field of Classification Search
 CPC ...... A61F 2/167; A61F 2/1678; A61F 2/1662; A61F 2/1667; A61F 2/1672; A61F 2/1675; A61F 2/1691; A61F 2/1664; A61F 2/16; A61F 2250/006; A61F 2002/1683; A61F 2002/1681; A61F 2002/1682; A61F 2002/16903; A61F 2002/16905; A61F 2002/169051; A61F 2002/169053

See application file for complete search history.

(56) References Cited

U.S. PATENT DOCUMENTS

| | | | |
|---|---|---|---|
| 9,314,373 B2 * | 4/2016 | Kudo | A61F 9/0008 |
| 9,364,316 B1 | 6/2016 | Kahook et al. | |
| 2009/0036898 A1 * | 2/2009 | Ichinohe | A61F 2/1678 |
| | | | 606/107 |
| 2017/0319332 A1 | 11/2017 | Kahook et al. | |

FOREIGN PATENT DOCUMENTS

DE 10201310518 A1 11/2014

* cited by examiner

*Primary Examiner* — Erich G Herbermann (57) ABSTRACT

Systems, methods, and devices, for delivery of a lens portion of a modular intraocular lens into an eye, may be provided. A device may include a housing; a nozzle positioned at an end of the housing, wherein an interior of the nozzle comprises a floor, the floor including an aperture; and a cam-actuated mechanism positioned within the housing, comprising: a lens stop comprising a base and a post, wherein the post is movably disposed within the aperture; and a slider configured to move in a direction toward the lens stop, wherein the lens stop is positioned at a distal end of the slider, the slider comprising a slot that is aligned with a portion of the base of the lens stop and configured to receive the portion of the base as the slider moves.

14 Claims, 11 Drawing Sheets

CAM-ACTUATED OPTIC LOCKOUT MECHANISM

TECHNICAL FIELD

The present disclosure generally relates to eye surgery and, more particularly, embodiments may generally relate to systems, methods, and devices for inserting an intraocular lens (IOL) into an eye that employ a cam-actuated optic lockout mechanism.

BACKGROUND

The human eye can suffer a number of maladies causing mild deterioration to complete loss of vision. While contact lenses and eyeglasses can compensate for some ailments, ophthalmic surgery may be required for others. Generally, ophthalmic surgery may be classified into posterior segment procedures, such as vitreoretinal surgery, and anterior segment procedures, such as cataract surgery. Vitreoretinal surgery may address many different eye conditions, including, but not limited to, macular degeneration, diabetic retinopathy, diabetic vitreous hemorrhage, macular hole, detached retina, epiretinal membrane, and cytomegalovirus retinitis.

For cataract surgery, a surgical procedure may require incisions and insertion of tools within an eye to replace the clouded lens with an intraocular lens (IOL). An insertion tool can be used for delivery of the IOL into the eye. By way of example, the insertion tool may include a plunger for forcing the IOL out of the nozzle of the insertion tool. In some instances, the IOL may be pre-loaded in the insertion tool. In other instances, a separate bay may be loaded into the insertion tool. The plunger may engage the IOL to advance the IOL from the bay, through the nozzle, and into the eye. The bay (or insertion tool) may include a folding chamber configured to cause the IOL to fold, for example, when the IOL advances through the folding chamber. In some instances, a separate action may cause folding of the IOL.

Delivery of the IOL from the insertion tool can be a multi-step process. For example, the delivery may include two stages, which may be referred to as an advancing stage and a delivery stage. In the advancing stage, the IOL can be advanced from a storage position in the bay to a dwell position. The IOL may be pre-folded or may be folded when advanced from the storage position to the dwell position. At the dwell position, advancement of the IOL may be halted. the nozzle positioned in the eye, the IOL may then be further advanced from the dwell position, in the delivery stage, which may include advancing the IOL through the nozzle and into the eye.

SUMMARY

In an exemplary embodiment, the present disclosure provides an apparatus for delivery of a lens portion of a modular intraocular lens into an eye. The apparatus includes a housing; a nozzle positioned at an end of the housing, wherein an interior of the nozzle comprises a floor, the floor including an aperture; and a cam-actuated mechanism positioned within the housing, comprising: a lens stop comprising a base and a post, wherein the post is movably disposed within the aperture; and a slider configured to move in a direction toward the lens stop, wherein the lens stop is positioned at a distal end of the slider, the slider comprising a slot that is aligned with a portion of the base of the lens stop and configured to receive the portion of the base as the slider moves.

In another exemplary embodiment, the present disclosure provides an apparatus for delivery of a lens portion of a modular intraocular lens into an eye. The apparatus includes a housing; a nozzle positioned at an end of the housing, wherein an interior of the nozzle comprises a floor, the floor including an aperture; and a cam-actuated mechanism comprising a lens stop comprising a base and a post, wherein the post is movably disposed within the aperture; a slider configured to move in a direction toward the lens stop, wherein the lens stop is positioned at a distal end of the slider, the slider including a slot that is aligned with a portion of the base of the lens stop and configured to receive the portion of the base as the slider moves; and a locking mechanism comprising a movable tab positioned within a recess of the housing, wherein the movable tab is adjacent to the slider and abuts the slider, wherein the recess comprises edges to confine the tab within the recess, wherein the tab is configured to move away from the slider thereby unlocking the slider and allowing axial movement of the slider.

In another exemplary embodiment, the present disclosure provides a method for unlocking an insertion tool for delivery of a lens portion of a modular intraocular lens into an eye. The method includes providing an insertion tool into the eye, wherein the insertion tool comprises a housing, wherein the nozzle is positioned at an end of the housing, wherein an interior of the nozzle comprises a floor, the floor including an aperture; and a cam-actuated mechanism positioned within the housing, comprising: a lens stop comprising a base and a post, wherein the post is movably disposed within the aperture; and a slider configured to move in a direction toward the lens stop, wherein the lens stop is positioned at a distal end of the slider, the slider including a slot that is aligned with a portion of the base of the lens stop and configured to receive the portion of the base as the slider moves. The method further includes moving the slider in the direction toward the lens stop; receiving the portion of the lens stop within the slot; and moving the post within the aperture.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

These drawings illustrate certain aspects of some of the embodiments of the present disclosure and should not be used to limit or define the disclosure.

DETAILED DESCRIPTION

For the purposes of promoting an understanding of the principles of the present disclosure, reference will now be made to the implementations illustrated in the drawings and specific language will be used to describe them. It will nevertheless be understood that no limitation of the scope of the disclosure may be intended. Any alterations and further modifications to the described devices, instruments, methods, and any further application of the principles of the present disclosure are fully contemplated as would normally occur to one skilled in the art to which the disclosure relates. In particular, it may be fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

Embodiments may generally relate to eye surgery. More particularly, embodiments may generally relate to systems, methods, and devices for folding or rolling an intraocular lens (IOL) for delivery into a patient's eye. In the process of delivery, the IOL may be folded and compressed into a symmetric hemispherical shape.

In at least one embodiment, the IOL may be modular. Embodiments of a modular IOL may include a base portion and a lens portion. The lens portion may be coupled to the base portion to form the modular IOL. In particular embodiments, the lens portion may not include haptics. The lack of haptics may make it difficult to ensure that the lens portion does not rotate about its centroid axis. Embodiments are directed to folding the lens portion that may not have haptics.

Embodiments may ensure that the IOL is located correctly in the nozzle as well as ensuring that the IOL does not rotate during folding. The homogeneity of the IOL's centroid allow the IOL to be folded successfully using symmetric features that apply equal and opposite forces. In certain embodiments, the IOL may include a short rhomboid spring at a leading edge and a tab at a trailing edge; this is in contrast with most 1-piece lenses which usually have long C or L shaped haptics. Once folded, the IOL may be kept in the folded configuration adhering to ISO 11979-3 standard. Embodiments may differ from previous delivery systems in that a lens fold occurs exclusively in a nozzle of the insertion tool instead of a lens bay of the insertion tool. This prevents features within a lens bay from interfering with the folding of the IOL. As such, there may be a need for a lock-out mechanism which may ensure that the IOL does not inadvertently become dislodged at any point prior to delivery. Due to the lock-out being cam actuated, there may not be an external lock or tab. Thus, there is one less part to discard in the sterile field during a procedure.

Embodiments may include a lock out mechanism including lens stop posts that may protrude from a bottom surface of an insertion tool upwards to a height higher than a thickness of the IOL. This may reduce or prevent scratching of the IOL during seating/installation or removal of the IOL. Further, the lens stop posts may provide guidance for loading the IOL. Each post may have a sufficient height to control movement in the horizontal, vertical and rotational axes. Due to the posts protruding from the bottom surface, when unlocked, the posts may drop down creating a flat floor for the IOL to traverse without interference.

Figure 1:
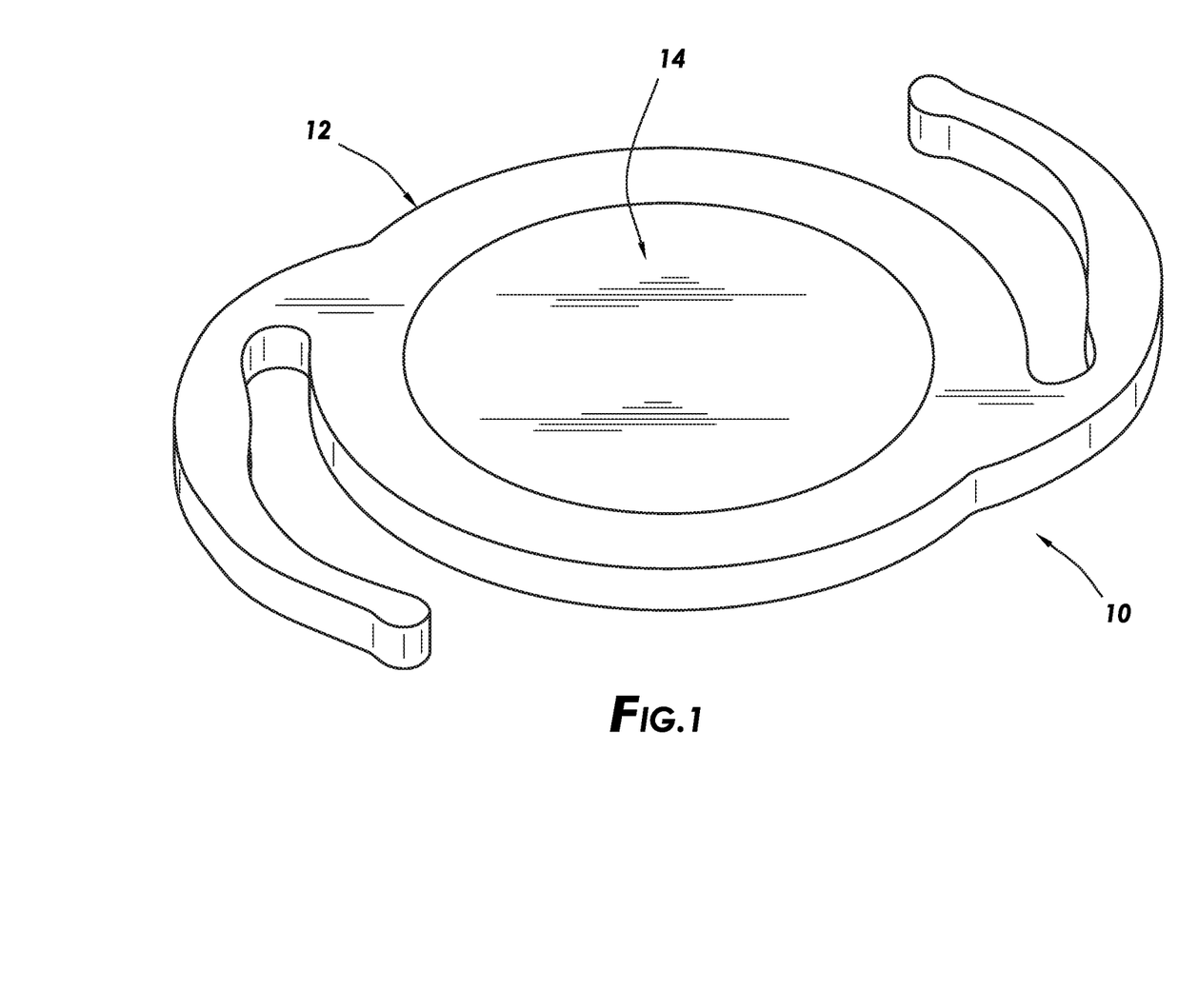
FIG. 1 illustrates a modular IOL with a lens portion positioned in a base portion in accordance with embodiments of the present disclosure.

FIG. 1 illustrates an embodiment of a modular IOL 10. The modular IOL 10 may be any suitable modular interocular lens. As illustrated, the modular IOL 10 may include a base portion 12 and a lens portion 14. In the illustrated embodiment, the lens portion 14 is positioned in the base portion 12. In operation, the modular IOL 10 can allow for the lens portion 14 to be modified or adjusted while leaving the base portion 12 in place, either intra-operatively or post-operatively. By way of example, the modular IOL 10 may be implanted into an eye. After implantation, the lens portion 14 may be modified, adjusted, and/or replaced while leaving the base portion 12 positioned in the eye. In at least one embodiment, the modular IOL 10 may be assembled in the eye. For example, the base portion 12 may first be implanted in the eye. The lens portion 14 may then be delivered into the eye and attached to the base portion 12.

Figure 2:
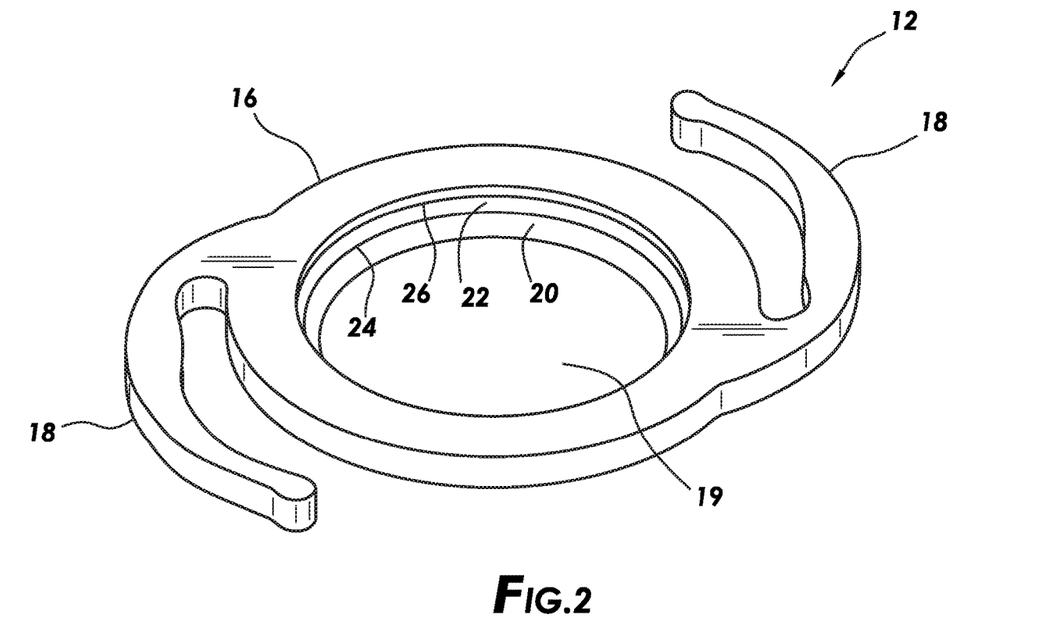
FIG. 2 illustrates a base portion of a modular IOL in accordance with embodiments of the present disclosure.

FIG. 2 illustrates the base portion 12 of the modular IOL 10 of FIG. 1 in accordance with particular embodiments of the present disclosure. In the illustrated embodiment, the base portion 12 includes a base 16 and haptic extensions 18. The haptic extensions 18 may be side struts (or other suitable extensions) extending from the base 16 that may stabilize the base portion 12 when it may be disposed within the patient's eye. In the illustrated embodiment, the base 16 may define a hole 19, which may be centrally located in the base 16 as shown on FIG. 2. While the hole 19 is shown as a through hole extending through the base 16, embodiments also contemplate hole 19 being a blind hole that does not extend through the base 16. For example, the base 16 may be a solid disc with the hole 19 being a blind hold that does not extend through the base 16, rather than an annular ring with the hole 19 extending through the base 16. Hole 19 may be defined by inner perimeter surface 20 of the base 16. In at least one embodiment, a recessed groove 22 is formed in inner perimeter surface 20. Recessed groove 22 may include a lower rim 24 and an upper rim 26. The upper rim 26 may have an insider diameter that is the same as or greater than the outside diameter of the lens portion 14 (excluding protrusions 30 shown on FIG. 3) such that the lens portion 14 can rest inside the hole 19 of the base 16. All or a portion of the lower rim 24 can have an inside diameter that is less than the outside diameter of the lens portion 14 (excluding protrusions 30 shown on FIG. 3) such that the lower rim 24 can act as a ledge or backstop for the lens portion 14 when placed in the hole 19 of the base 16. The base portion 12 may be unitary or may be formed from component parts that are combined or attached in any suitable manner.

Figure 3:
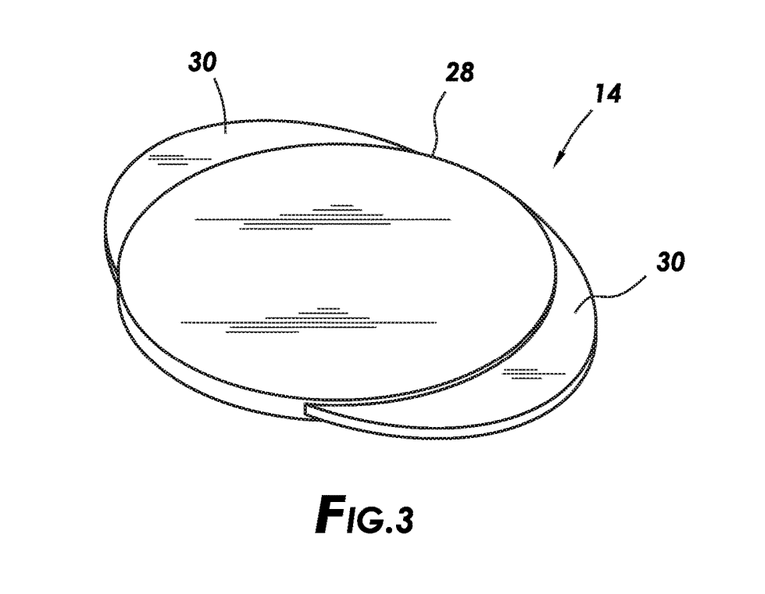
FIG. 3 illustrates a lens portion of a modular IOL in accordance with embodiments of the present disclosure.

With reference to FIG. 3, the lens portion 14 of the modular IOL 10 of FIG. 1 is illustrated in accordance with particular embodiments of the present disclosure. In the illustrated embodiments, the lens portion 14 includes an optic portion 28 and one or more protrusions 30. While FIG. 3 illustrates two of the protrusions 30, embodiments may include only one of the protrusions 30 or alternatively three, four, or more of the protrusions 30. In addition, the protrusions 30 on the lens portion 14 may be the same or different from one another. The protrusions 30 are shown as being fixed to the optic portion 28; however, it should be understood that one or more of the protrusions 30 may be actuated to move from a compressed position for delivery into the hole 19 of the base 16 (e.g., shown on FIG. 2) to an uncompressed extended position for deployment into the recessed groove 22 of the base 16 (e.g., shown on FIG. 2), thus forming an interlocking connection between the base portion 12 and the lens portion 14. The outside curvature of the protrusions 30 may have a radius conforming to the inside radius of the recessed groove 22. This arrangement should limit relative movement between the base portion 12 and the lens portion 14 once connected. In embodiments, a suitable optic portion 28 may be in a shape similar to that of a natural lens within the eye and made from a suitable material such as silicone, acrylic, and/or combinations thereof. While the optic portion 28 is shown as being circular, the optic portion 28 may be any suitable shape, such as oval or ellipsoidal, for example, with the protrusions 30 positioned adjacent the long axis. This arrangement would thus define a gap between the edge of the optic portion 28 along its short axis and the inner perimeter surface 20 in the base 16. The gap may enable access for a probe or similar device to pry apart the lens portion 14 from the base portion 12 if separation were needed.

Figure 4:
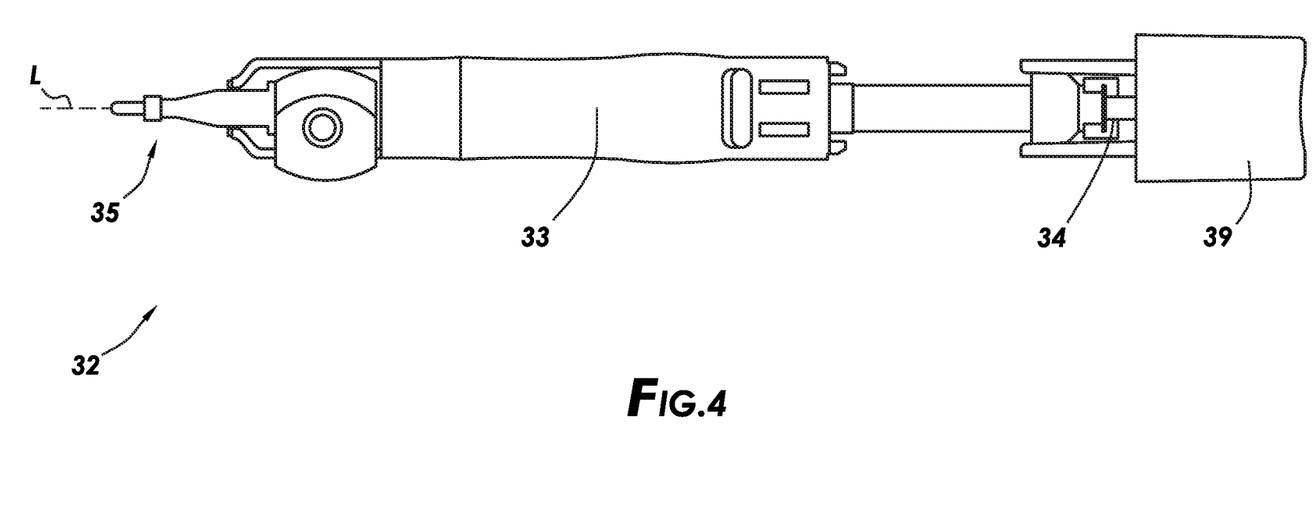
FIG. 4 is a top view of an insertion tool in accordance with embodiments of the present disclosure.

FIG. 4 illustrates a top view of an insertion tool 32 in accordance with exemplary embodiments. The insertion tool 32 may include a housing 33, a plunger 34 at least partially disposed axially within the housing 33, and a nozzle 35. The plunger 34 is slidably disposed within the housing 33 and may move axially along a longitudinal axis of the housing 33. A plunger head 39 may be coupled to the plunger 34 and may be positioned exterior to the housing 33. The nozzle 35 may be disposed on end of the insertion tool 32 that is opposite to the plunger head 39, as shown. In other words, the plunger 34 and the plunger head 39 may extend from a first end of the housing 33, and the nozzle 35 may extend from a second opposite end of the housing 33, as shown. A user may depress the plunger head 39 to move the plunger 34 axially (toward the nozzle 35) within the housing 33. The housing 33 may be configured to receive the nozzle 35. In some embodiments, the nozzle 35 may be attachable the housing 33 so that the nozzle 35 can be coupled and decoupled from the housing 33. In other embodiments, the nozzle 35 (or a portion thereof) may be integrally formed in or a permanent part of the housing 33.

Figure 5:
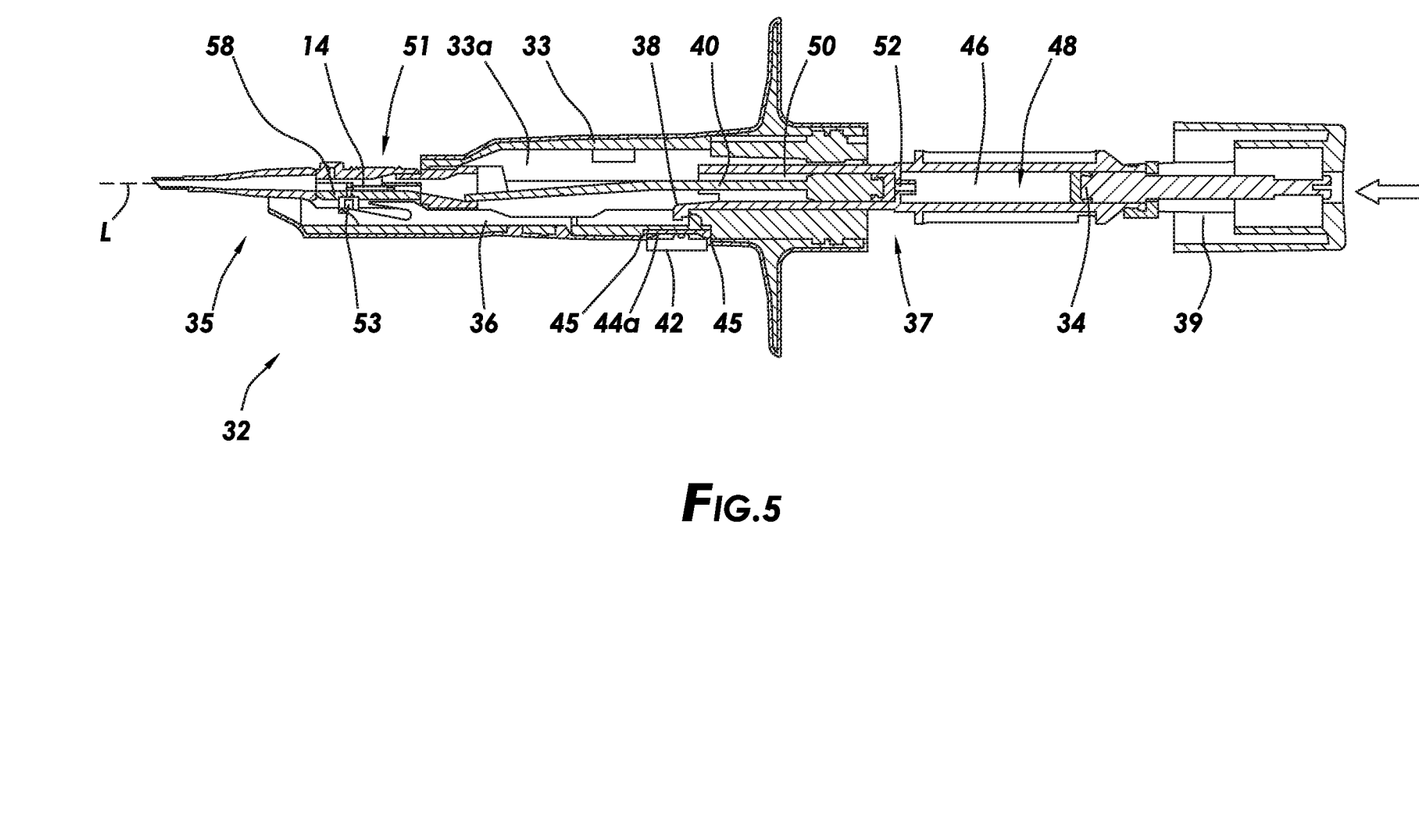
FIG. 5 is a cross-section of the top view of the insertion tool of FIG. 4 in accordance with embodiments of the present disclosure.

FIG. 5 is a cross-section of the top view of the insertion tool 32 of FIG. 4 in accordance with particular embodiments. The cross-section is taken in a downward direction along the entire length of the insertion tool 32. As shown, the insertion tool 32 includes a slider 36 that may be a rigid structure (e.g., an elongated member). The slider 36 may be coupled to a member 38 that extends from a plunger assembly 37. The plunger assembly 37 may be movably disposed within the insertion tool 32 (e.g., a passage 33a of an interior portion of the housing 33). The plunger assembly 37 may move axially toward the nozzle 35 upon depression of the plunger 34.

The plunger assembly 37 may include the plunger 34, and a first cylinder 48 in fluid communication with a second cylinder 50 via an orifice 52, and a shaft 40 that may be movably disposed within the second cylinder 50. The plunger 34 may be depressed in a direction (see arrow) toward the nozzle 35 to force a hydraulic fluid 46 from the first cylinder 48 into the second cylinder 50 via the orifice 52, as shown. This causes the hydraulic fluid 46 to propel the shaft 40 through the nozzle 35 to contact and push the lens portion 14 through the nozzle 35 and into a patient's eye. The lens portion 14 may be positioned within the nozzle 35 of the insertion tool 32. In certain embodiments, the protrusions 30 of the lens portion 14 may include a rhomboid spring 41 at a leading end (of the lens portion 14) and a tab 43 (e.g., extending at 90° from the base of the lens portion 14) at a trailing end of the lens portion 14, as shown on FIG. 7, for example. In certain embodiments, the plunger assembly 37 may also axially move toward the nozzle 35 upon depression of the plunger 34.

A tab 42 may be a locking mechanism that can be pulled away from the member 38. The tab 42 may be slidably positioned within a recess 44a of the housing 33. In a locked position, the tab 42 extends into grooves of the slider 36 or abuts the slider 36 thereby preventing axial movement of the slider 36 and the plunger assembly 37, upon depression of the plunger 34. When in an unlocked position (as shown), the tab 42 is pulled away from the member 38 thereby allowing axial movement of the slider 36 and the plunger assembly 37, upon depression of the plunger 34.

The tab 42 may move in a direction orthogonal to the longitudinal axis L. The tab 42 may be confined to the recess 44a by edges 45 or grooves within the recess 44a. In certain embodiments, the tab 42 cannot be pulled out completely away from the insertion tool 32. The lack of a completely removable lock provides a benefit of one less part to discard in a sterile field during a procedure.

Figure 6:
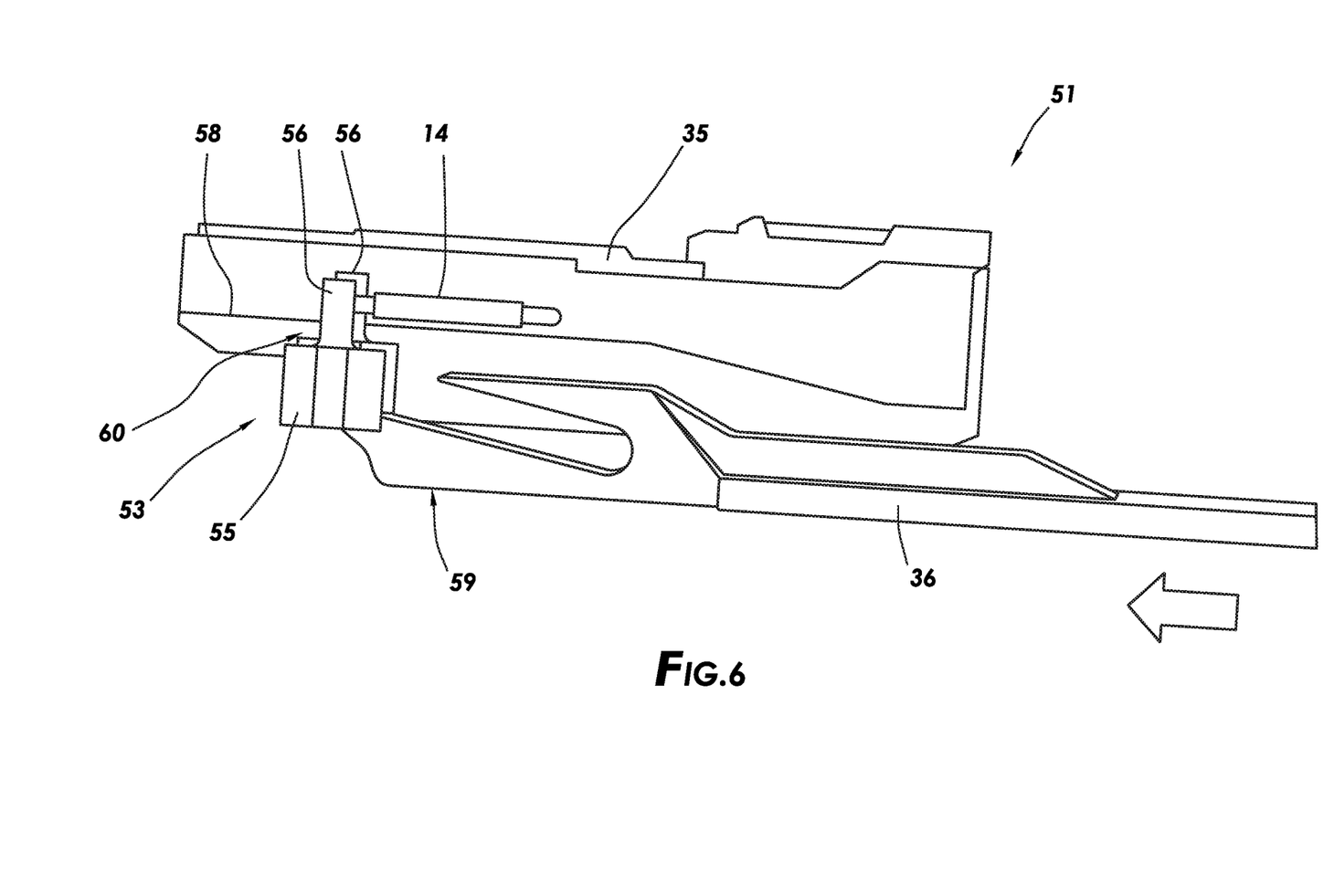
FIG. 6 illustrates a front portion of the cross-section of the insertion tool of FIG. 5 in accordance with embodiments of the present disclosure.
Figure 7:
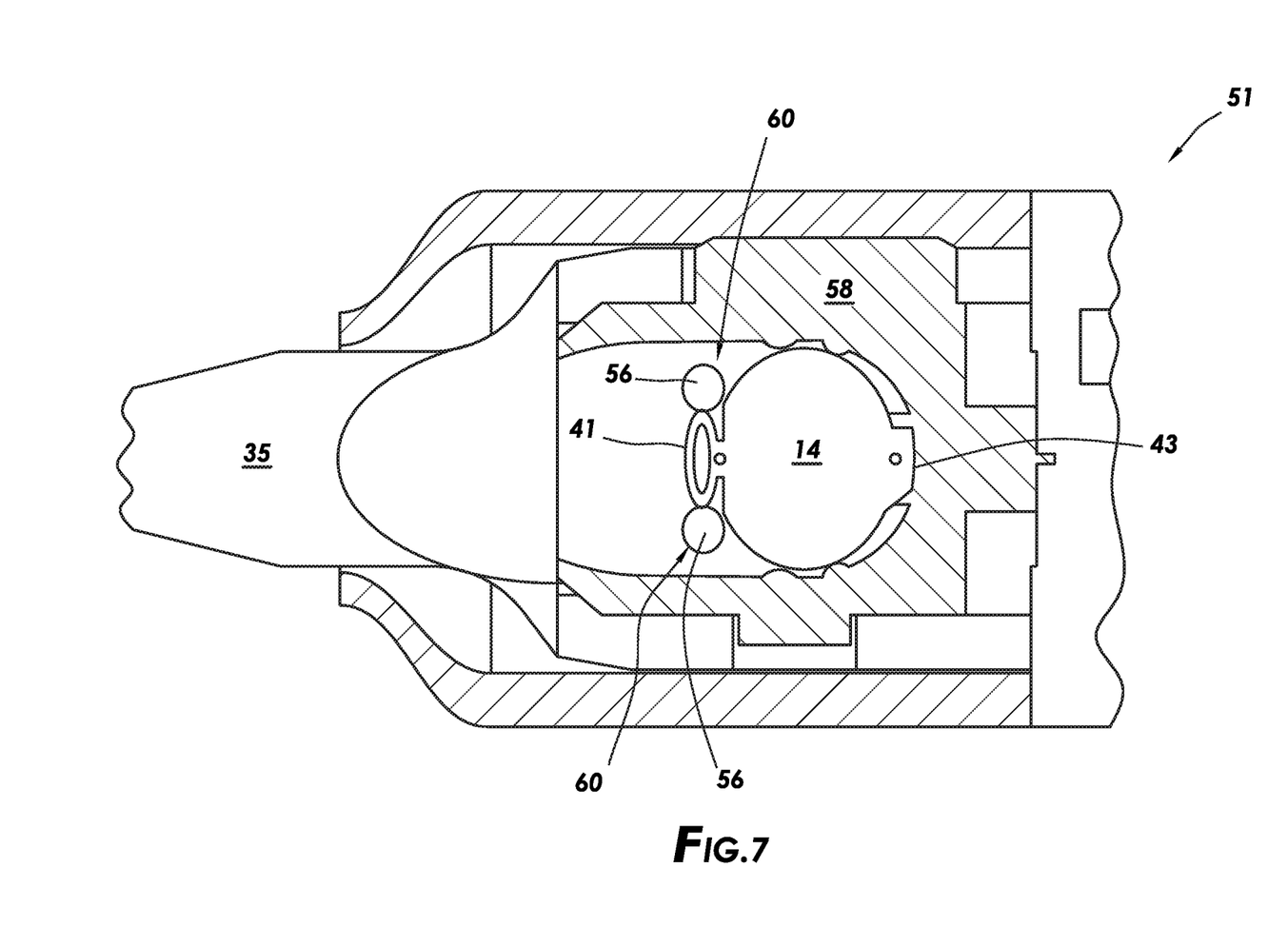
FIG. 7 is a top plan view of the front portion of FIG. 6 in accordance with embodiments of the present disclosure.
Figure 8:
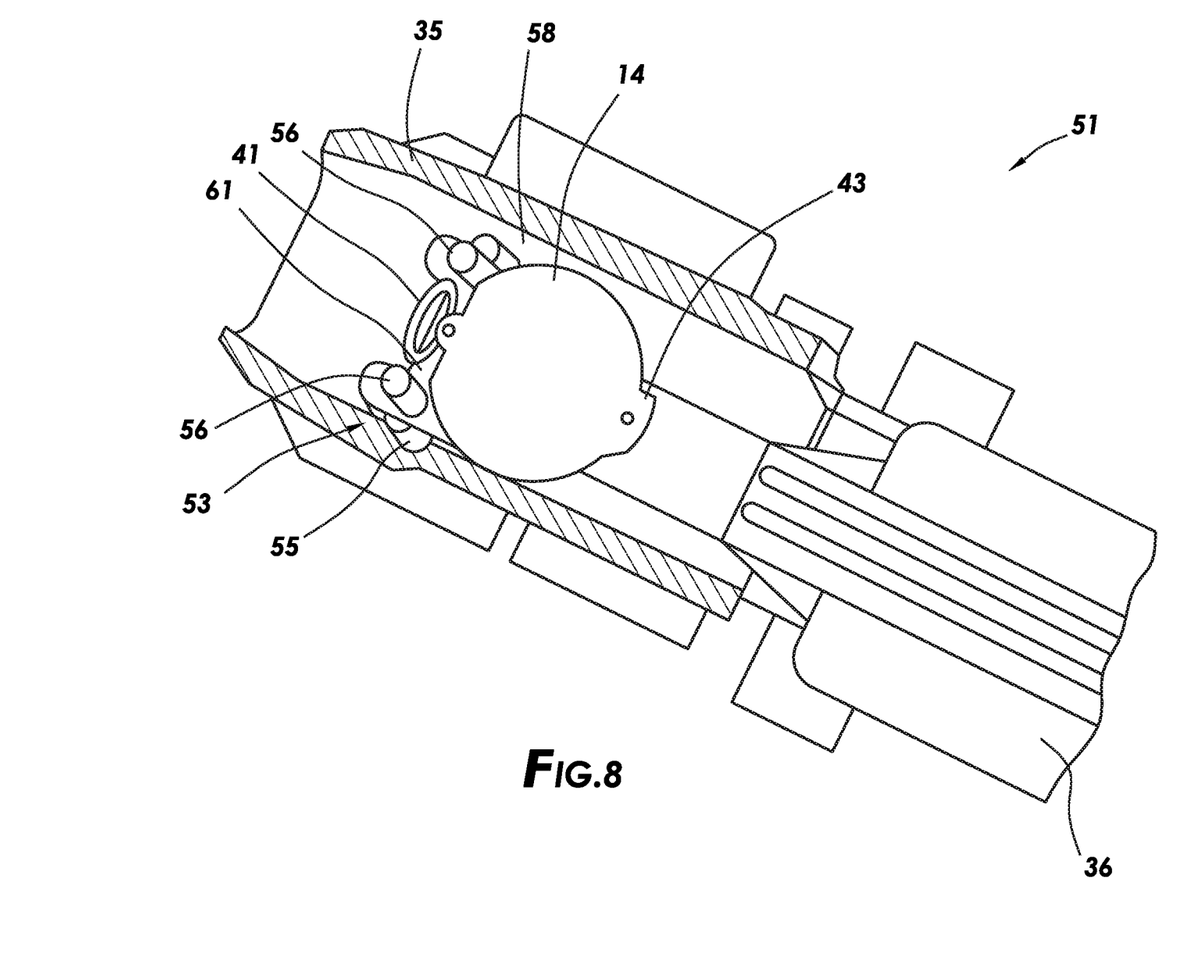
FIG. 8 is a perspective top plan view of the front portion of FIG. 6 in accordance with embodiments of the present disclosure.

FIGS. 6-8 illustrate multiple views of a front portion 51 of the insertion tool 32 of FIG. 5 in accordance with particular embodiments. The insertion tool 32 may also include a lens stop 53 including a base 55 and posts 56 configured as a stop for the lens portion 14 when the posts 56 are in a lock-out position.

In the lock-out position, the posts 56 may protrude orthogonally from a floor 58 within the nozzle 35 thereby preventing axial movement of the lens portion 14. The lens stop 53 may be positioned to contact a distal end 59 of the slider 36.

The distal end 59 of the slider 36 may extend in a direction toward the lens stop 53 and in between the posts 56 (as shown on FIGS. 6 and 8, for example). The posts 56 may be elongated members configured to move through apertures 60 in the floor 58 upon axial movement of the slider 36. That is, as the slider 36 moves toward the nozzle 35, the distal end 59 may engage the lens stop 53 and pull or move the posts 56 through the apertures 60 and away from the lens portion 14 (e.g., the posts 56 may be in a retracted position). In certain embodiments, portions of the posts 56 remain in the apertures 60 thereby filling the apertures 60 and creating a continuous flat and smooth surface (without interruptions), within the floor 58, for the lens portion 14 to traverse, as shown on FIG. 7 for example. The lens portion 14 may be positioned on the floor 58 and adjacent to the apertures 60. In an extended or lock-out position, the posts 56 protrude through the apertures 60 and abut the leading end of the lens portion 14 to prevent axial movement of the lens portion 14, as shown on FIG. 6, for example. Also, shown on FIG. 6 is a direction of axial movement of the slider 36 upon depression of the plunger 34, indicated by an arrow.

Figure 9A:
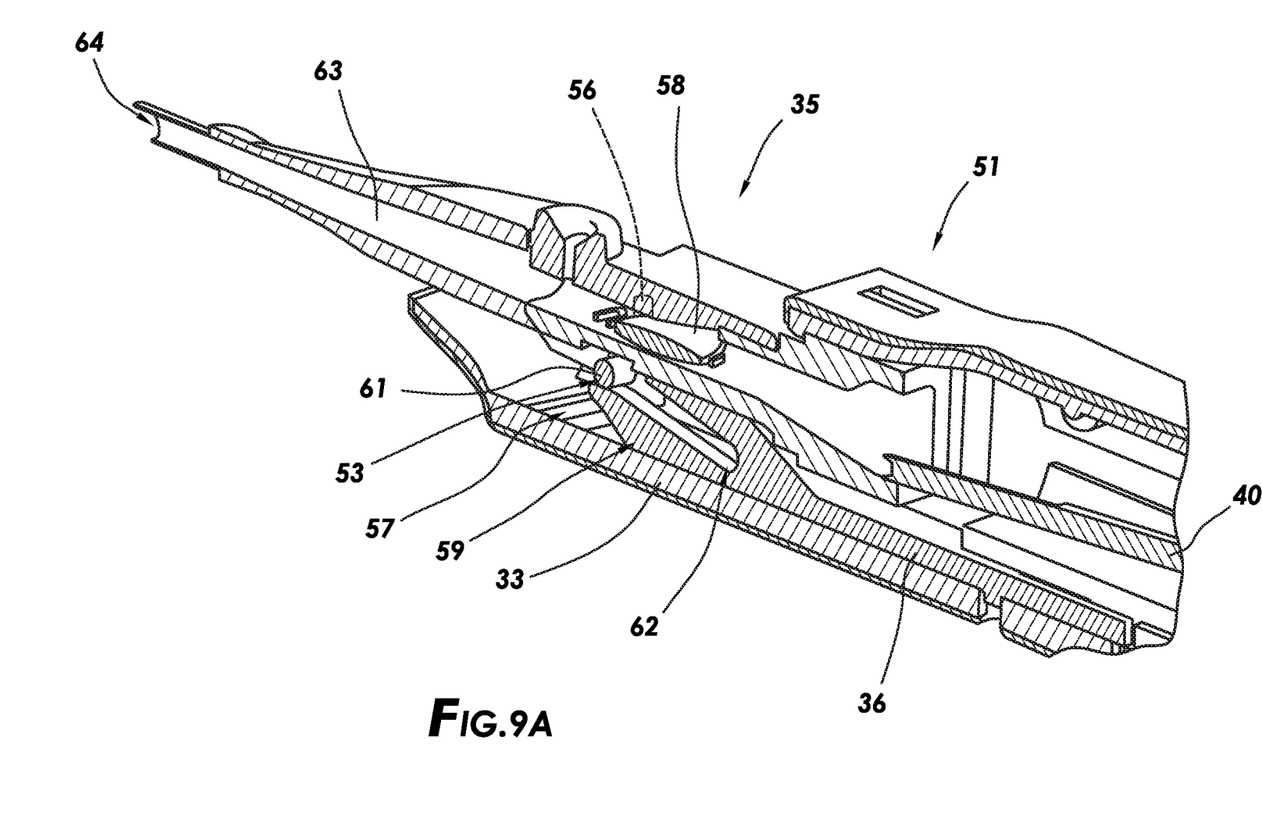
FIG. 9A is a side perspective view of the front portion of FIG. 6 of the insertion tool in a lock-out position in accordance with embodiments of the present disclosure.

As shown on FIG. 9A, in the lock-out position, the plunger 34 has not been depressed and the slider 36 has not moved axially forward. Upon depression of the plunger 34, the slider 36 may move along track 57 positioned within the housing 33, as shown.

Figure 9B:
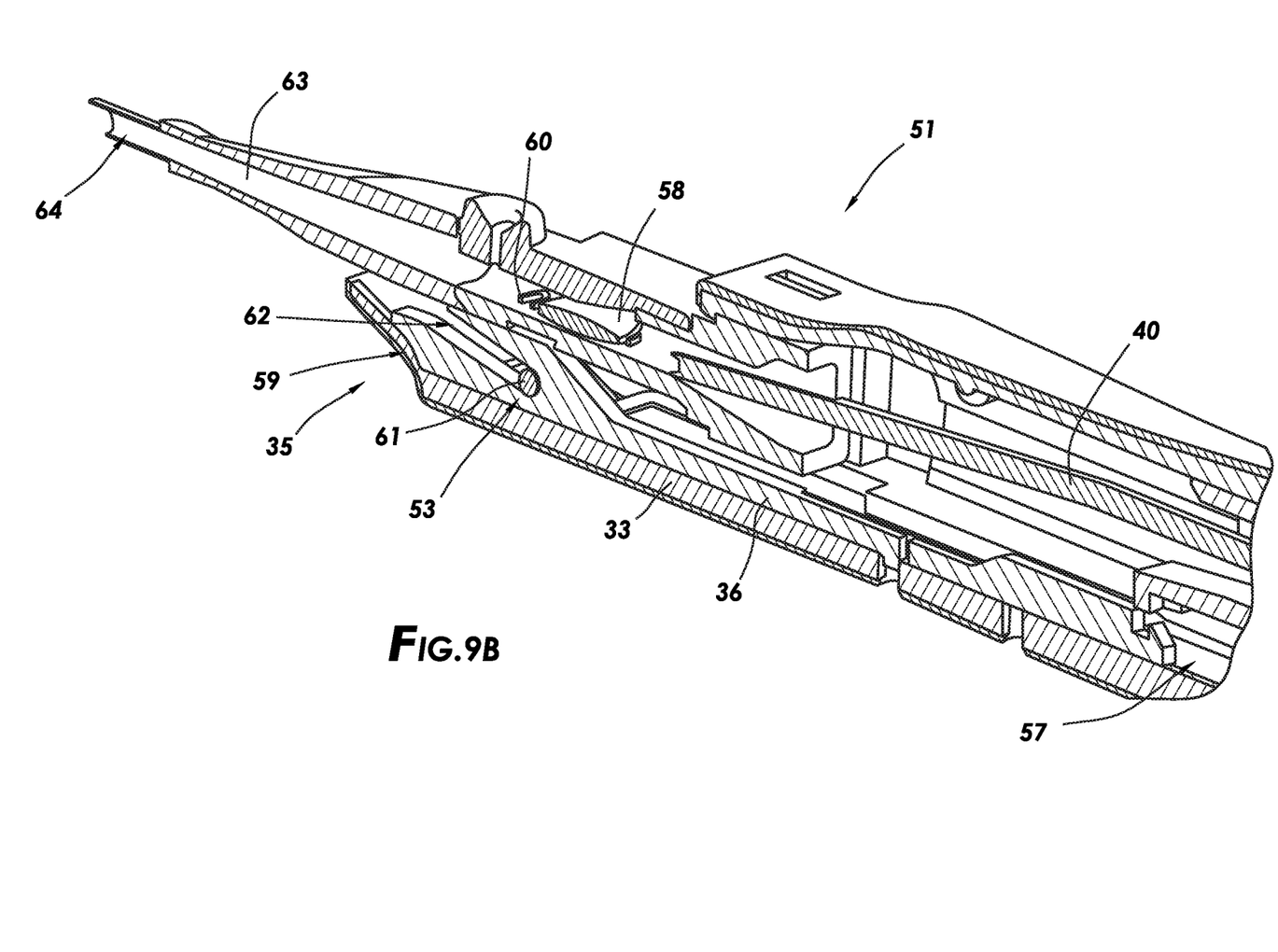
FIG. 9B is a side perspective view of the front portion of FIG. 6 of the insertion tool in an unlocked position in accordance with embodiments of the present disclosure.

As shown on FIG. 9B, in an unlocked position, the slider 36 may move forward and contact a portion 61 of the base 55 that extends between the posts 56 of the lens stop 53. The portion 61 may be an elongated member (e.g., of a cylindrical shape) and is configured to enter into a slot 62 located at the distal end 59 of the slider 36, upon the slider 36 moving forward. A thickness of the portion 61 may be less than a width of the slot 62, for example. The portion 61 is also illustrated on FIG. 8.

As the slot 62 receives the portion 61, the lens stop 53 is moved or pulled away (e.g., downward) away from the lens portion 14. The slot 62 may be angled (e.g., 15° to 75° relative to a longitudinal axis of the slider 36), as shown, to move or force the lens stop 53 to move away from the lens portion 14 via the apertures 60 and into the slot 62, as shown. The slot 62 of the slider 36 may receive the lens stop 53, as the plunger 34 and/or the plunger assembly 37 is depressed. As the plunger 34 is depressed, the shaft 40 moves forward to move the lens portion 14 through the nozzle 35 and into the patient's eye.

In certain embodiments, the insertion tool 32 may be preloaded. That is, when provided to an end-user, the insertion tool 32 may have the lens portion 14 (e.g., modular IOL 10, base portion 12, and/or lens portion 14) in an unfolded state already present there within and ready to deliver. Having the insertion tool 32 preloaded with the lens portion 14 should reduce the number of steps a user may be required to accomplish before delivering the lens portion 14 into a patient's eye. With a reduced number of steps, error and risk associated with delivery of the lens portion 14 may be reduced. Further, an amount of time required to deliver the lens portion 14 may also be reduced. In some embodiments, the lens portion 14 may be pre-loaded into the nozzle 35.

In an initial position (e.g., a dwell position), the lens portion 14 may be positioned in the nozzle 35. In some embodiments, the lens portion 14 may be folded in the nozzle 35. That is, the lens portion 14 may be rolled or folded to reduce a size of the lens portion 14. This reduction in size allows delivery of the lens portion 14 through a minimally sized incision in the eye.

In the deployment stage, the plunger 34 may advance the lens portion 14 from the dwell position in the nozzle 35, through a deployment channel 63 of the nozzle 35 and out through an aperture 64 of the nozzle 35 into a patient's eye.

An exemplary technique for implantation of the modular IOL 10 into an eye 65 of a patient will now be described with respect to FIGS. 10A-10C.

Figure 10A:
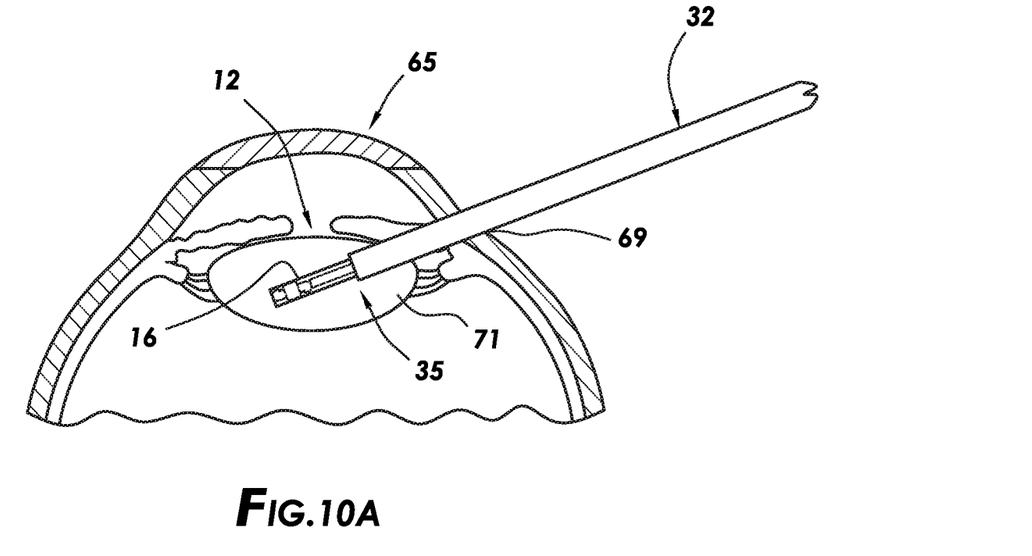
FIGS. 10A-10C illustrate implantation of a modular IOL in accordance with embodiments of the present disclosure.
Figure 10B:
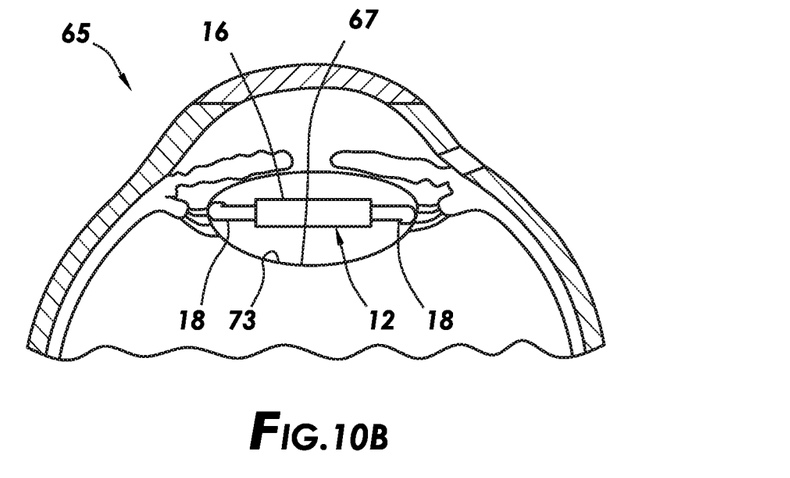

As illustrated on FIG. 10A, the insertion tool 32 may first dispense the base portion 12 into the eye 65 of a patient. In embodiments, an incision 69 may be made in the eye 65 by a surgeon. For example, the incision 69 may be made through the sclera 67 of the eye 65. The incision 69 may be a suitable width or length. Without limitation, the suitable width and/or length may be less than about 4000 microns (4 millimeters). For example, the incision 69 may have a suitable width and/or length of from about 1000 microns to about 400 microns, from about 1000 microns to about 3000 microns, or from about 2000 microns to about 3000 microns. After the incision 69 is made, the nozzle 35 of the insertion tool 32 may be inserted through the incision 69 into an interior portion 71 of the eye 65. The insertion tool 32 may be actuated to dispense the base portion 12 into a capsular bag 73 of the eye 65. This initial movement of the base portion 12 may be performed at any suitable time, for example, before the incision 69 is made. Once the insertion tool 32 is positioned with the nozzle 35 in the eye 65, the insertion tool 32 may then drive the base portion 12 (in a folded or rolled configuration) through the nozzle 35 and into the interior portion 71 of the eye 65. Upon dispensation, the base portion 12 should unfurl and settle within the capsular bag 73 of the eye 65, as shown on FIG. 10B. The haptic extensions 18 may be manipulated, for example, to engage the inside an equator of the capsular bag 73. The haptic extensions 18 may engage the capsular bag 73 to secure the base portion 12 in the capsular bag 73.

Figure 10C:
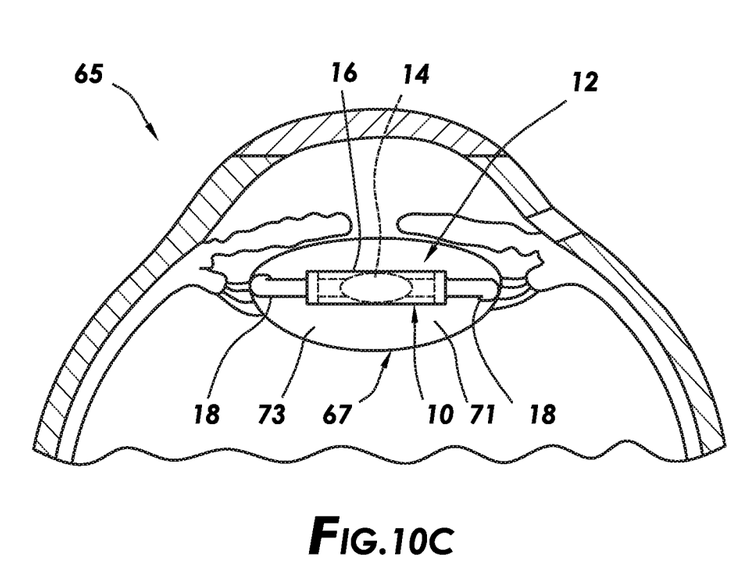

As illustrated on FIG. 10C, the lens portion 14 may be positioned in the interior portion 71 of the eye 65. In the illustrated embodiment, the lens portion 14 is shown positioned in the base 16 of the base portion 12. The lens portion 14 may be delivered in a folded (or rolled configuration) and allowed to unfurl after ejection from the insertion tool 32. The lens portion 14 may be positioned in the base 16 of the base portion 12 and secured to the base portion 12, for example, by use of the protrusions 30 shown on FIG. 3, to form the modular IOL 10. However, embodiments should not be limited to use of the protrusions 30 for interlocking the lens portion 14 and the base portion 12 and other suitable locking mechanisms may be used for securing lens portion 14 to the base portion 12 for forming the modular IOL 10. The base portion 12 may hold the lens portion 14 within the eye 65 so that the lens portion 14 may refract light to be focused on the retina.

Use of the methods and systems described herein may provide numerous benefits and advantages over other IOL delivery systems. For example, the insertion tools including the preloaded IOL, as described herein, improve sterility due to decreased handling by users. Additionally, the insertion tools may be utilized to constrain the IOL during shipping, storage and any operation prior to delivery. Users may be able to locate an exact loading position for the IOL. The cam mechanism may be useful for providing non-removable lockout mechanisms. The concept of initially locking and then folding and compressing the IOL and then transferring the IOL to a location where it can be advanced and delivered may be applicable to IOL delivery systems in single and multi-piece lens implantation techniques and designs.

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:

1. An apparatus for delivery of a lens portion of a modular intraocular lens into an eye, comprising: a housing; a nozzle positioned at an end of the housing, wherein an interior of the nozzle comprises a floor, the floor including an aperture; and a cam-actuated mechanism positioned within the housing, comprising: a lens stop comprising a base and a post, wherein the post is movably disposed within the aperture; and a slider configured to move in a direction toward the lens stop, wherein the lens stop is positioned at a distal end of the slider, the slider comprising a slot that is aligned with a portion of the base of the lens stop and configured to receive the portion of the base as the slider moves, wherein the lens stop is configured in a lock-out position, the lock-out position comprising the post protruding through the aperture and wherein a leading end of the lens portion abuts the post that is protruding through the aperture thereby preventing axial movement of the lens portion.

2. The apparatus of claim 1, wherein the lens stop is configured in a retracted position, the retracted position comprising an end of the post positioned flush with the floor to form a continuous surface with the floor to allow traversal of the lens portion along the floor.

3. The apparatus of claim 2, wherein the retracted position further comprises the portion of the base of the lens stop positioned in the slot of the slider, wherein the slider is in an axially extended position and wherein the post is moved away from the lens portion.

4. The apparatus of claim 3, wherein the slot of the slider is angled to receive the portion of the base.

5. The apparatus of claim 4, further comprising the lens portion, wherein the lens portion is positioned on the floor adjacent to the aperture.

6. The apparatus of claim 5, wherein the lens portion comprises a rhomboid spring at a leading end of the lens portion, wherein the leading end is adjacent to the aperture.

7. The apparatus of claim 6, wherein the lens portion further includes a tab extending at a trailing end of the lens portion, wherein the trailing end is opposite to the leading end.

8. The apparatus of claim 7, wherein the tab extends at a right angle.

9. The apparatus of claim 8, wherein the lens portion does not include haptics.

10. An apparatus for delivery of a lens portion into an eye, comprising: a housing; a nozzle positioned at an end of the housing, wherein an interior of the nozzle comprises a floor, the floor including an aperture; and a cam-actuated mechanism comprising: a lens stop comprising a base and a post, wherein the post is movably disposed within the aperture; a slider configured to move in a direction toward the lens stop, wherein the lens stop is positioned at a distal end of the slider, the slider including a slot that is aligned with a portion of the base of the lens stop and configured to receive the portion of the base as the slider moves; and a locking mechanism comprising a movable tab positioned within a recess of the housing, wherein the movable tab is adjacent to the slider and abuts the slider, wherein the recess comprises edges to confine the tab within the recess, wherein the tab is configured to move away from the slider thereby unlocking the slider and allowing axial movement of the slider, wherein the lens stop is configured in a lock-out position, the lock-out position comprising the post protruding through the aperture.

11. The apparatus of claim 10, further comprising the lens portion, wherein a leading end of the lens portion abuts the post that is protruding through the aperture thereby preventing axial movement of the lens portion.

12. The apparatus of claim 10, wherein the lens stop is configured in a retracted position, the retracted position comprising an end of the post positioned flush with the floor to form a continuous surface with the floor.

13. The apparatus of claim 12, wherein the retracted position further comprises the portion of the base of the lens stop positioned in the slot of the slider, wherein the slider is in an axially extended position and wherein the post is moved away from the lens portion.

14. The apparatus of claim 13, wherein the slot of the slider is angled to receive the portion of the base.

\* \* \* \* \*